(12) United States Patent
Garlow

(10) Patent No.: US 12,419,598 B2
(45) Date of Patent: Sep. 23, 2025

(54) COUNTERBALANCED IMAGING DEVICE

(71) Applicant: Medtronic Navigation, Inc., Louisville, CO (US)

(72) Inventor: David Adams Garlow, Lynnfield, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 257 days.

(21) Appl. No.: 18/156,967

(22) Filed: Jan. 19, 2023

(65) Prior Publication Data
US 2024/0245371 A1     Jul. 25, 2024

(51) Int. Cl.
*A61B 6/00*     (2024.01)

(52) U.S. Cl.
CPC ............ *A61B 6/447* (2013.01); *A61B 6/4435* (2013.01)

(58) Field of Classification Search
CPC ..... A61B 6/447; A61B 6/4435; A61B 6/4441; A61B 6/035; A61N 5/1081
See application file for complete search history.

(56) References Cited

U.S. PATENT DOCUMENTS

| | | | |
|---|---|---|---|
| 6,940,941 B2* | 9/2005 | Gregerson | A61B 6/4405 378/197 |
| 7,001,045 B2 | 2/2006 | Gregerson et al. | |
| 7,108,421 B2 | 9/2006 | Gregerson et al. | |
| 7,338,207 B2 | 3/2008 | Gregerson et al. | |
| 7,490,982 B2 | 2/2009 | Gregerson et al. | |
| 7,905,659 B2 | 3/2011 | Gregerson et al. | |
| 8,308,361 B2 | 11/2012 | Gregerson et al. | |
| 8,746,973 B2* | 6/2014 | Gregerson | A61B 6/02 378/197 |
| 9,700,272 B2* | 7/2017 | Gregerson | A61B 5/055 |
| 10,869,643 B2* | 12/2020 | Gregerson | A61B 5/055 |
| 11,504,081 B2* | 11/2022 | Gregerson | A61B 6/032 |
| 2003/0235266 A1* | 12/2003 | Gregerson | A61N 5/1082 378/4 |
| 2004/0013239 A1* | 1/2004 | Gregerson | A61B 6/4405 378/197 |

(Continued)

FOREIGN PATENT DOCUMENTS

| | | |
|---|---|---|
| WO | WO 03/103496 | 12/2003 |
| WO | WO 2004/017832 | 3/2004 |
| WO | WO 2021/252625 | 12/2021 |

OTHER PUBLICATIONS

International Search Report and Written Opinion for International (PCT) Patent Application No. PCT/IB2024/050485, dated Mar. 13, 2024, 11 pages.

*Primary Examiner* — David P Porta
*Assistant Examiner* — Gisselle M Gutierrez
(74) *Attorney, Agent, or Firm* — Sheridan Ross P.C.

(57) ABSTRACT

A counterbalanced imaging device is provided and includes an imaging source and an imaging detector. The counterbalanced imaging device also includes a gantry ring that physically supports the imaging source and the imaging detector. The gantry ring also enables the imaging source and the imaging detector to simultaneously rotate about a center of rotation. The gantry ring may also comprise a detachable segment having one or more counterbalance measures contained therein to align a center of gravity of the gantry ring with the center of rotation when the detachable segment is mounted onto the gantry ring.

20 Claims, 10 Drawing Sheets

(56) References Cited

U.S. PATENT DOCUMENTS

| | | | |
|---|---|---|---|
| 2004/0022350 A1* | 2/2004 | Gregerson | A61B 6/4405 378/15 |
| 2006/0120511 A1* | 6/2006 | Gregerson | A61B 6/4429 378/198 |
| 2008/0212743 A1* | 9/2008 | Gregerson | A61B 6/035 378/197 |
| 2011/0200175 A1* | 8/2011 | Gregerson | A61N 5/1081 378/197 |
| 2016/0038109 A1 | 2/2016 | Fortuna et al. | |
| 2021/0068775 A1* | 3/2021 | Gregerson | A61B 6/4405 |
| 2023/0039962 A1* | 2/2023 | Gregerson | A61B 6/4447 |
| 2024/0188914 A1* | 6/2024 | Gregerson | A61B 5/704 |

* cited by examiner

COUNTERBALANCED IMAGING DEVICE

BACKGROUND

The present disclosure is generally directed to an imaging device, and relates more particularly to a counterbalanced imaging device.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

A counterbalanced imaging device according to at least one embodiment of the present disclosure comprises a gantry ring having a central axis and an opening that provides access to the central axis, the gantry ring having an interior cavity contained therein; a C-shaped rotor housed within the interior cavity, and rotatable around the central axis, wherein the C-shaped rotor causes the imaging device to have a center of gravity offset from the central axis of the gantry ring; a detachable segment of the gantry that selectively covers the opening, wherein a portion of the detachable segment comprises one or more weights to counterbalance the C-shaped rotor thereby moving a center of gravity of the C-shaped rotor and the detachable segment towards the central axis of the gantry ring; a drive mechanism secured to the rotor, and adapted to rotate the rotor around the interior of the gantry ring; an imaging source secured to the rotor at a first position; and an imaging detector secured to rotor at a second position, opposite the source on the gantry ring.

Any aspect herein, wherein the detachable segment comprises a door and a sector gear, wherein the sector gear is configured to attach to the rotor when the detachable segment is attached to the gantry ring and configured to attach to the door when the detachable segment is not attached to the gantry ring.

Any aspect herein, wherein the portion of the detachable segment comprises the sector gear.

Any aspect herein, wherein the sector gear comprises a first sector gear and a second sector gear.

Any aspect herein, wherein the imaging source is configured to project radiation as the source rotates about the central axis, and wherein the imaging detector is positioned to detect the projected radiation.

Any aspect herein, wherein the gantry ring is configured to be positioned around an object to be imaged.

Any aspect herein, wherein an object to be imaged may enter and exit the gantry ring through the opening.

Any aspect herein, wherein the imaging source is an X-ray source.

Any aspect herein, wherein the weight is attached to the portion of the detachable segment.

Any aspect herein, wherein the weight is integrated with the portion of the detachable segment.

A counterbalanced imaging device according to at least one embodiment of the present disclosure comprises a gantry ring having a central axis and an opening that provides access to the central axis, the gantry ring having an interior cavity contained therein; a detachable segment of the gantry that selectively covers the opening; a C-shaped rotor housed within the interior cavity, and rotatable around the central axis, wherein the C-shaped rotor extends from a first end to a second end, and wherein each of the first end and the second end has one or more counterbalance measures contained therein to align a center of gravity of the C-shaped rotor with the center of rotation; a drive mechanism secured to the rotor, and adapted to rotate the rotor around the interior of the gantry ring; an imaging source secured to the rotor at a first position; and an imaging detector secured to rotor at a second position, opposite the source on the gantry ring.

Any aspect herein, wherein the counterbalance measures comprise weights attached to each of the first end and the second end.

Any aspect herein, wherein the counterbalance measures comprise weights integrated into each of the first end and the second end.

Any aspect herein, wherein the imaging source is an X-ray source.

An imaging device according to at least one embodiment of the present disclosure comprises an imaging source; an imaging detector; and a gantry ring that physically supports the imaging source and the imaging detector and that enables the imaging source and the imaging detector to simultaneously rotate about a center of rotation, wherein the gantry ring comprises a detachable segment having one or more counterbalance measures contained therein to align a center of gravity of the gantry ring with the center of rotation when the detachable segment is mounted onto the gantry ring.

Any aspect herein, wherein the detachable segment comprises a door and a sector gear.

Any aspect herein, wherein the counterbalanced measures comprise the sector gear.

Any aspect herein, wherein the sector gear comprises a first sector gear and a second sector gear.

Any aspect herein, wherein each of the first sector gear and the second sector gear comprises steel.

Any aspect herein, wherein the imaging source is configured to project radiation as the source rotates about the central axis, and wherein the imaging detector is positioned to detect the projected radiation.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
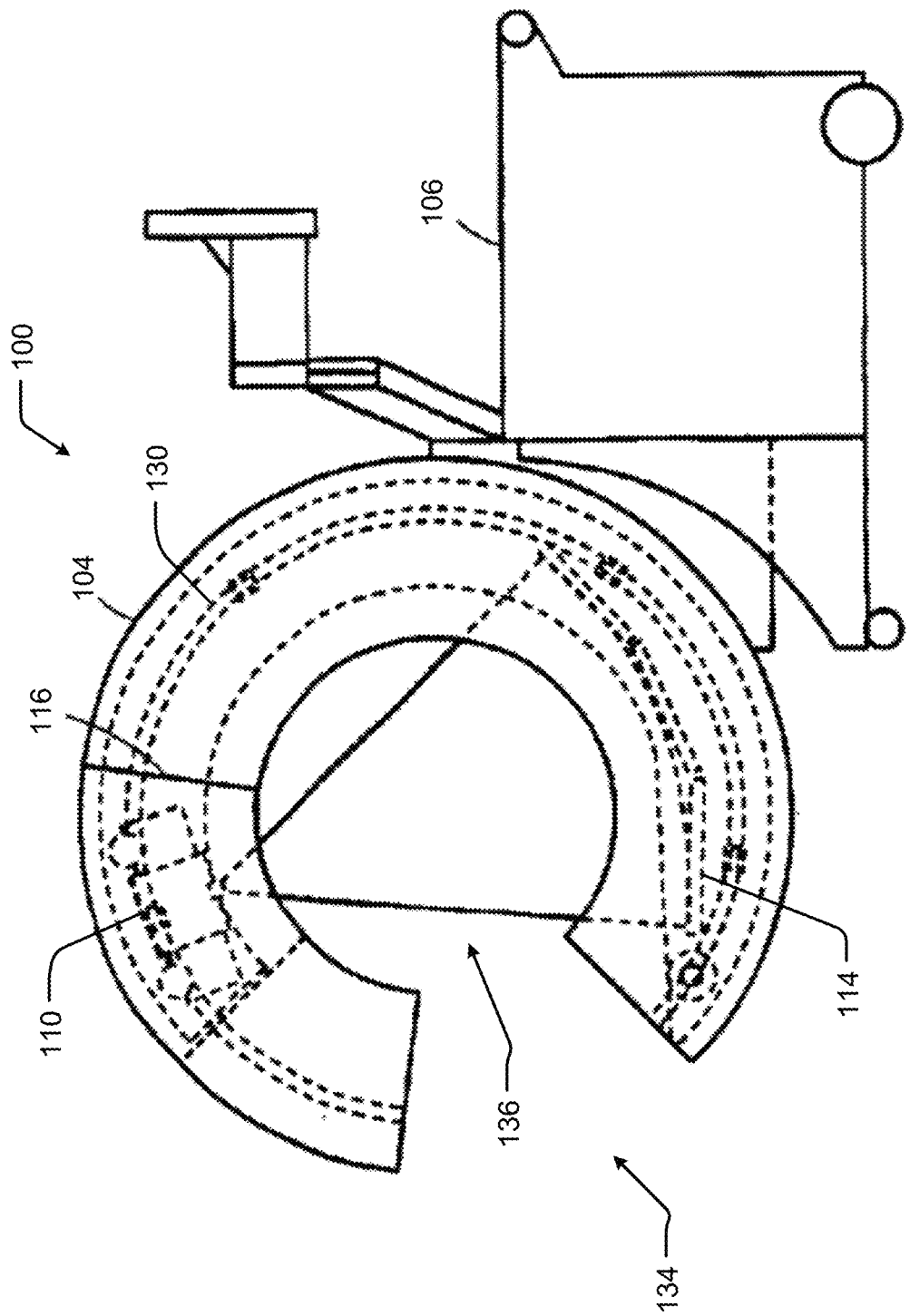
FIG. 1 is a schematic diagram of an imaging device according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

In a conventional CT X-ray scanning system, an object being imaged (typically a patient) enters an imaging area lengthwise from either the front or rear of a gantry (i.e. along a central axis of the gantry opening). This makes it difficult to employ CT X-ray scanning during many medical procedures where a CT X-ray scanning application is desirable and helpful, such as during surgery. Also, the conventional CT X-ray scanner is a relatively large, stationary device having a fixed bore, and is typically located in a dedicated X-ray room, such as in the radiology department of a hospital. CT scanning devices are generally not used in a number of environments, such as emergency departments, operating rooms, intensive care units, procedure rooms, ambulatory surgery centers, physician offices, and on the military battlefield due to the size and difficulty in employing the CT scanning device.

Embodiments of the present disclosure include an O-arm scanning system in which a rotor of the O-arm is "C" shaped. The O-arm scanning system also includes a door to allow the O-arm, once the door is opened, the ability to straddle the patient and/or operating table and subsequently close the door, thereby encircling the patient. Thus, the O-arm allows a "breakable" gantry to encircle a patient and/or table in the operating room. A consequence of the rotor being "C" shaped is that it is not balanced about a center of rotation of the O-arm. As the rotor rotates, the center of gravity of the O-arm shifts with the rotor, causing the O-arm to deflect in the vertical direction by about 0.040 inches. This variation of the O-arm position in the vertical direction results in image degradation.

In at least one embodiment of the present disclosure, counterbalancing weights can be placed at the top and bottom of the "C" of the rotor using a heavy material. In other embodiments, a portion of the "breakable" segment of the gantry may be adjusted. For example, a sector gear of the segment may be manufactured out of steel (which is about three times the weight of aluminum). The sector gear is configured to attach from the door to the rotor when the breakable segment is attached to the gantry. Alternatively or additionally, a second sector gear may be added opposite the first sector gear as needed. Such configuration may provide a much lighter net rotor weight, can be easily packaged, and counterbalance the rotor.

Embodiments of the present disclosure provide technical solutions to one or more of the problems of (1) counterbalancing an O-arm imaging device with a detachable segment, (2) aligning a center of gravity of an imaging device with a center of rotation of the imaging device, and (3) improving image data quality of image data obtained from an O-arm imaging device with a detachable segment.

Figure 2:
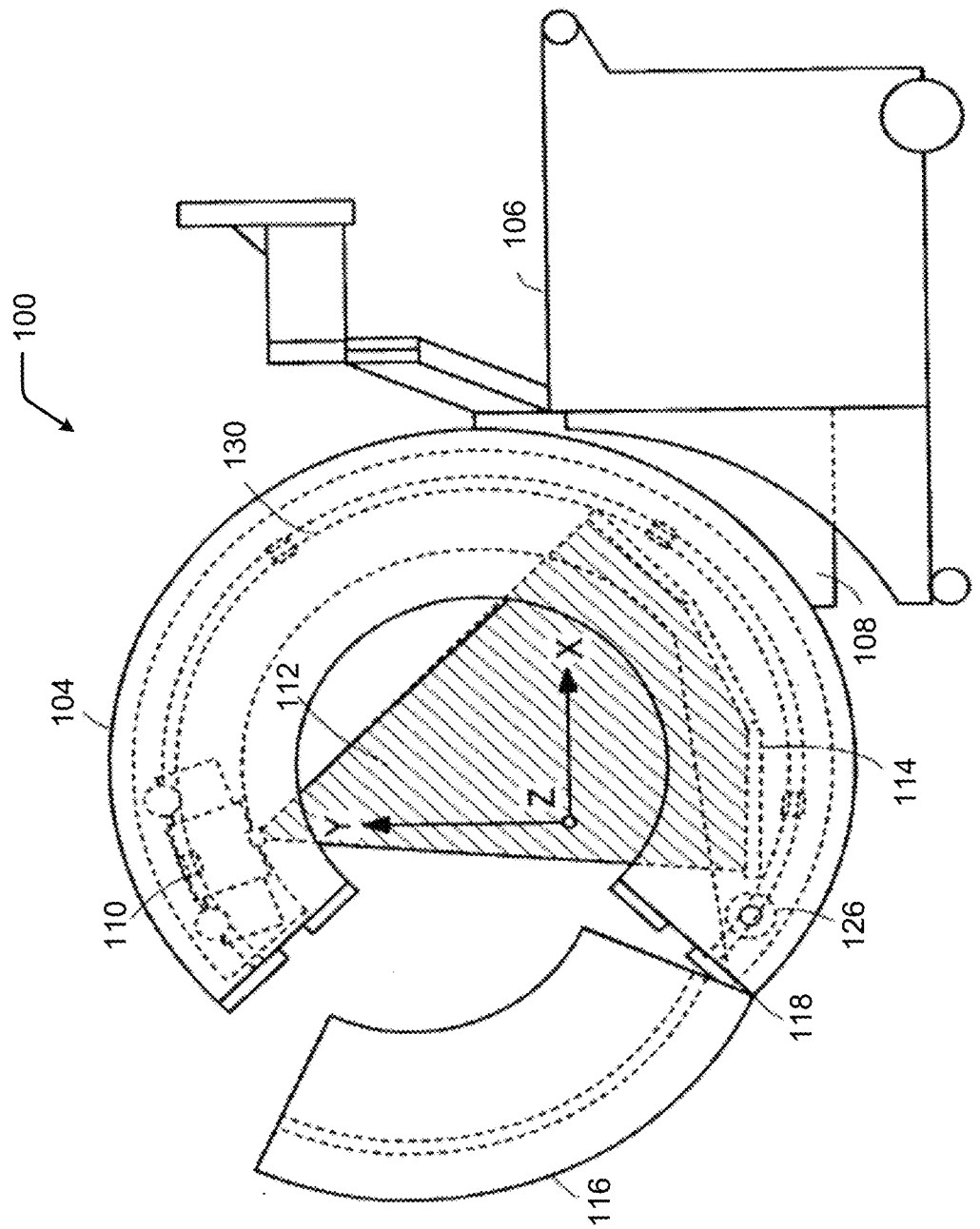
FIG. 2 is a schematic diagram of an imaging device according to at least one embodiment of the present disclosure.

FIGS. 1 and 2 are each a schematic diagram showing an imaging device 100. The imaging device 100 may comprise an X-ray scanning system such as an X-ray scanning system as described in U.S. Pat. No. 6,940,941, filed Feb. 15, 2002, which is hereby incorporated by reference in its entirety. The imaging device 100 described may be used for two-dimensional and/or three-dimensional scanning. For example, individual two-dimensional projections from set angles along a gantry rotation (as described below) can be viewed, or multiple projections collected throughout a partial or full rotation may be reconstructed using cone or fan beam tomographic reconstruction techniques.

The imaging device 100 includes a gantry 104 secured to a support structure, which could be, for example a mobile or stationary cart, a patient table, a wall, a floor, or a ceiling. As shown in FIG. 1, the gantry 104 is secured to a mobile cart 106 in a cantilevered fashion via a ring positioning unit 108. In certain embodiments, the ring positioning unit 108 enables the gantry 104 to translate and/or rotate with respect to the support structure, including, for example, translational movement along at least one of the x-, y-, and z-axes, and/or rotation around at least one of the x- and y-axes. Imaging devices with a cantilevered, multiple-degree-of-freedom movable gantry are described in U.S. Provisional Applications 60/388,063, filed Jun. 11, 2002, and 60/405,098, filed Aug. 21, 2002, the entire teachings of which are herein incorporated by reference. The mobile cart 106 can optionally include a power supply, an X-ray power generator, a computer system for controlling operation of the X-ray scanning device and for performing image processing, tomographic reconstruction, or other data processing functions, and/or a display system, which can include a user interface for controlling the device. It will be understood that one or more fixed units can also perform these functions.

Figure 4:
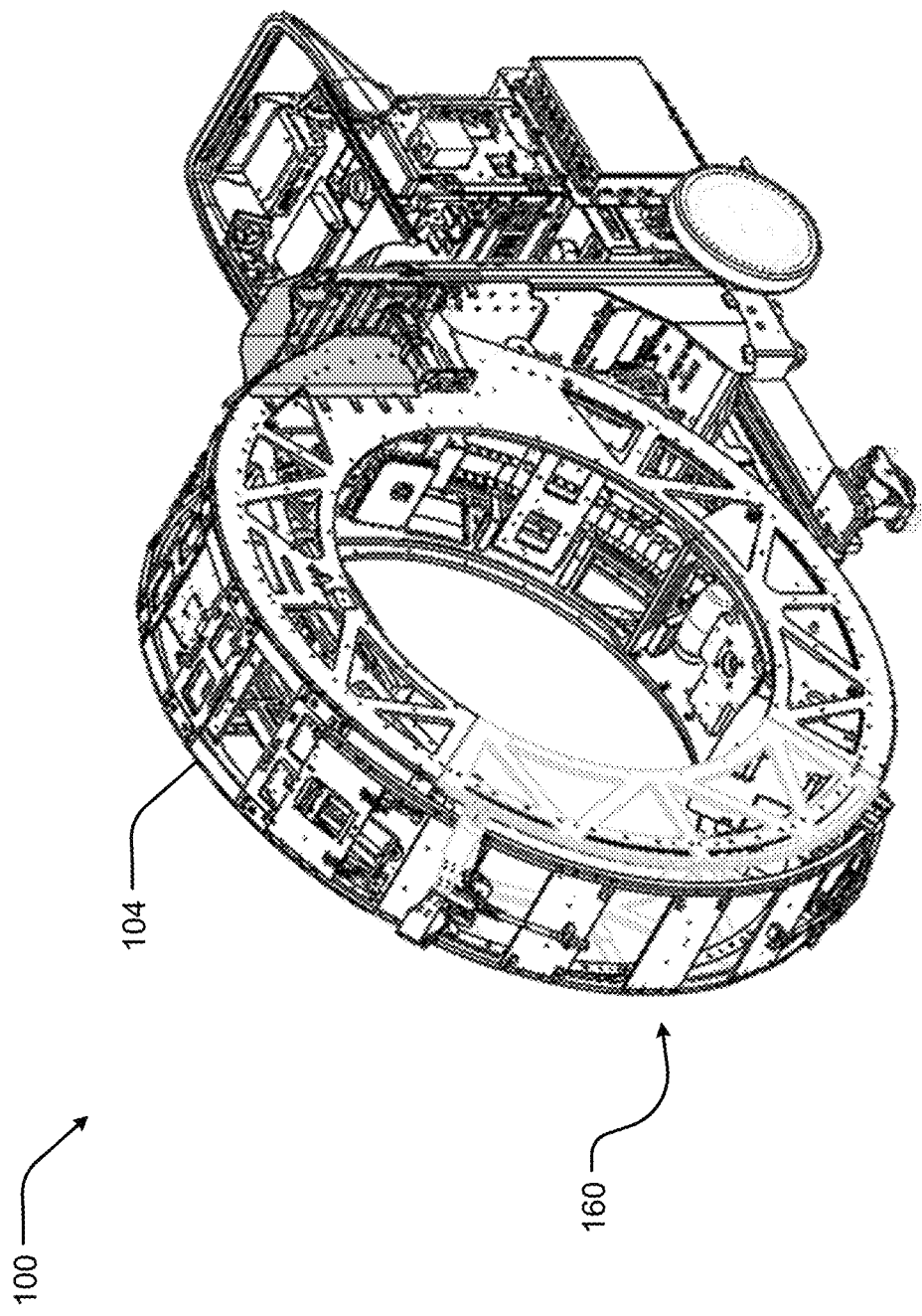
FIG. 4 is an isometric view of an imaging device according to at least one embodiment of the present disclosure.

The gantry 104 is a substantially circular, or "O-shaped," housing having a central imaging area 136 into which an object being imaged is placed. In other words, the gantry 104 may be positioned around an object to be imaged. It will be appreciated that in some embodiments the gantry 104 may also be referred to as a gantry ring 104. The gantry 104 includes an imaging source 110 positioned at a first position and an imaging detector 114 positioned at a second position opposite the imaging source 110. In some embodiments the imaging source 110 comprises an X-ray source such as, for example, a rotating anode pulsed X-ray source that projects a beam of X-ray radiation 112 into the central imaging area 136 of the gantry 104, through the object being imaged, and onto the imaging detector 114 located on the opposite side of the gantry 104. The imaging source 110 is also able to rotate 360 degrees around the interior of the gantry 104 via a rotor 124 (described in detail in FIG. 4) in a continuous or step-wise manner so that the X-ray beam 112 can be projected through the object at various angles. At each projection angle, the X-ray radiation beam 112 passes through and is attenuated by the object. The attenuated radiation is then detected by the imaging detector 114 opposite the imaging source 110. In at least one embodiment, the gantry 104 includes the imaging detector 114 that is configured to rotate around the interior of the gantry 104 in coordination with the rotation of the imaging source 110 via the rotor 124 so that, for each projection angle, the imaging detector 114 is positioned opposite the imaging source 110 on the gantry 104. The detected X-ray radiation from each of the projection angles can then be processed, using well-known reconstruction techniques, to produce a two-dimensional or three-dimensional object reconstruction image.

In some embodiments, the imaging detector 114 may comprise an array. For example, the imaging detector 114 may comprise three two-dimensional flat panel solid-state detectors arranged side-by-side, and angled to approximate the curvature of the gantry 104. It will be understood, however, that various detectors and detector arrays can be used with the imaging device 100, including any detector configurations used in typical diagnostic fan-beam or cone-beam CT scanners. For example, the imaging detector 114 may comprise a two-dimensional thin-film transistor X-ray detector using scintillator amorphous-silicon technology. For large field-of-view imaging, the imaging detector 114 can be translated to, and acquire imaging data at, two or more positions along a line or arc opposite the imaging source 110, such as via a motorized detector rail and bearing system. Examples of such imaging detectors 114 are described in commonly owned U.S. Provisional Application 60/366,062, filed Mar. 19, 2002, the entire teachings of which are incorporated herein by reference.

The gantry 104 also includes a segment 116 that at least partially detaches from the gantry 104 to provide an opening 134 or "break" in the gantry 104 through which the object to be imaged may enter and exit the central imaging area 136 of the gantry 104 in a radial direction. The segment 116 may also be referred to as a detachable segment 116. In the illustrated embodiment, the segment 116 is telescoping, which allows the segment 116 to detach from the gantry 104 and telescope over a portion of the gantry 104. In other words, the segment 116 can move laterally up and rotate over the gantry 104. In one embodiment, the segment 116 can be attached to the gantry 104 with alignment pins. A release mechanism releases the pins, and the sidewalls of the segment 116 translate outward relative to the gantry ring, thus allowing the segment 116 to telescope over the fixed upper portion of the gantry 118. The object being imaged (for instance, a patient) can then enter the gantry 104 from the opening 134 formed by the segment 116 detaching from and telescoping over the gantry 104 (as opposed to from the front or rear side of the gantry, as in conventional systems). The segment 116 can then be reattached to fully enclose the object within the gantry 104. Alternatively, or in addition, the gantry 104 (when the segment 116 is detached and the opening 134 is accessible) can be moved towards the object in a lateral direction to position the object within the central imaging area 136, and then the segment 116 can close around the object and attach to the gantry 104.

In addition to the telescoping door embodiment of FIG. 1, the gantry 104 can have various other embodiments such as, for example, a hinged segment 116. As shown in FIG. 2, the segment 116 of the gantry 104 is secured to the gantry 104 via a hinge 118 which allows the segment 116 to swing out like a door from a fully closed position to a fully open position. In each of these systems or any system using a detachable segment, the segment 116 of the gantry 104 at least partially detaches from the gantry 104 to provide the opening 134 or "break" in the gantry 104 through which the object to be imaged may enter and exit the central imaging area 136 of the gantry 104 in a radial direction. The segment 116 can then be reconnected to the gantry 104 to perform 2D X-ray or 3D tomographic X-ray imaging. In any embodiment of the segment 116, the segment 116 also includes a mechanism for securing the segment 116 in place in a closed gantry configuration, yet also permits the segment 116 to be easily detached to open or "break" the gantry 104.

Figure 3:
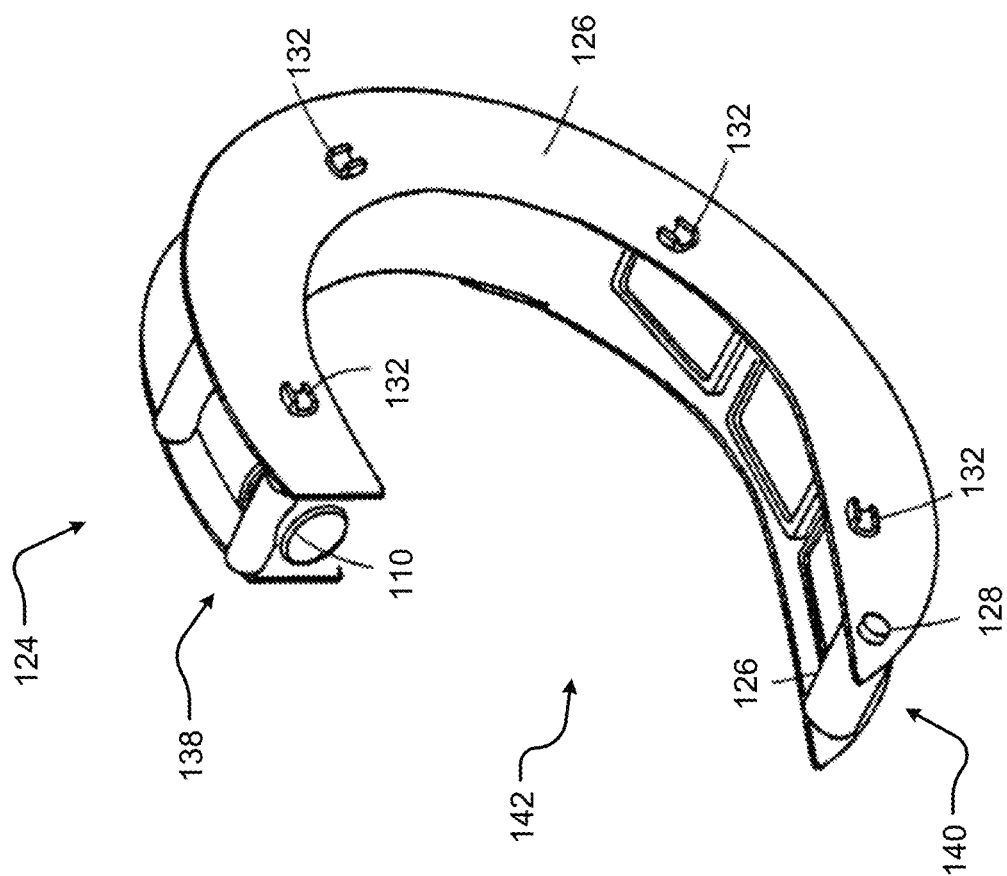
FIG. 3 is a tilted view of a rotor according to at least one embodiment of the present disclosure.

Turning to FIG. 3, a tilted view of the rotor 124 is shown. The rotor 124 may support the imaging source 110 and the imaging detector 114 within a rigid frame 126 designed to maintain a constant spacing between the imaging source 110 and imaging detector 114 as the rotor 124 rotates inside the gantry 104. The rotor 124 also includes a motor 126 and gear 128 for driving the rotor 124 around the interior of the gantry 104. As visible in FIGS. 1 and 2, interior side walls of the gantry 104 may include one or more rails 130 which extend in a continuous loop around the interior of the gantry 104 when the segment 116 of the gantry 104 is attached to the gantry 104. The gear 128 of the rotor assembly 124 contacts the rail 130 of the gantry 104, and uses the rail 130 to drive the rotor 124 around the interior of the gantry 104. The rotor 124 also includes corresponding rail carriages 132, which mate with the rails 130 of the gantry 104 to help guide the rotor 124 as it rotates inside the gantry 104.

In some embodiments, the rotor 124 is C-shaped and extends from a first end 138 to a second end 140, with an open region 142 at least as large as the opening 134 formed when the segment 116 is detached from the gantry 104. In such embodiments, due to the shape and weight of the rotor 124, the rotor 124 may cause a center of gravity 144 (as described below and shown in FIG. 4) of the imaging device 100 to shift from a central axis 146 of the gantry 104 when the segment 116 is attached to the gantry 104. In other words, the center of gravity 144 of the imaging device 100 may be offset from the central axis 146 (and thus, the center of rotation) of the imaging device 100. Thus, in some instances, as the rotor 124 rotates, the center of gravity 144 may shift with the rotor 124 and may cause center of gravity 144 to deflect in a vertical direction by about 0.040 inches, which may result in image degradation. As will be described in detail below, counterbalancing measures may be added to the imaging device 100 to counterweight the rotor 124, thereby improving image quality.

Turning to FIGS. 4-12, an example embodiment of the telescoping door is shown. It will be appreciated that in some embodiments the segment 116 comprises the door 160 and a sector gear 148 (shown in FIGS. 9-12). The door 160 and the sector gear 148 are configured to attach to and detach from the gantry 104 to provide the opening 134 to the central imaging area 136 of the gantry 104. During use of the imaging device 100, the sector gear 148 attaches to the rotor 124 when the segment 116 is attached to the gantry 104 and attaches to the door when the segment 116 is not attached to the gantry 104. In other words, the sector gear 148 is attached to the rotor 124 when the opening 134 to the gantry 104 is closed and is attached to the door when the opening 134 to the gantry 104 is opened.

Figure 5:
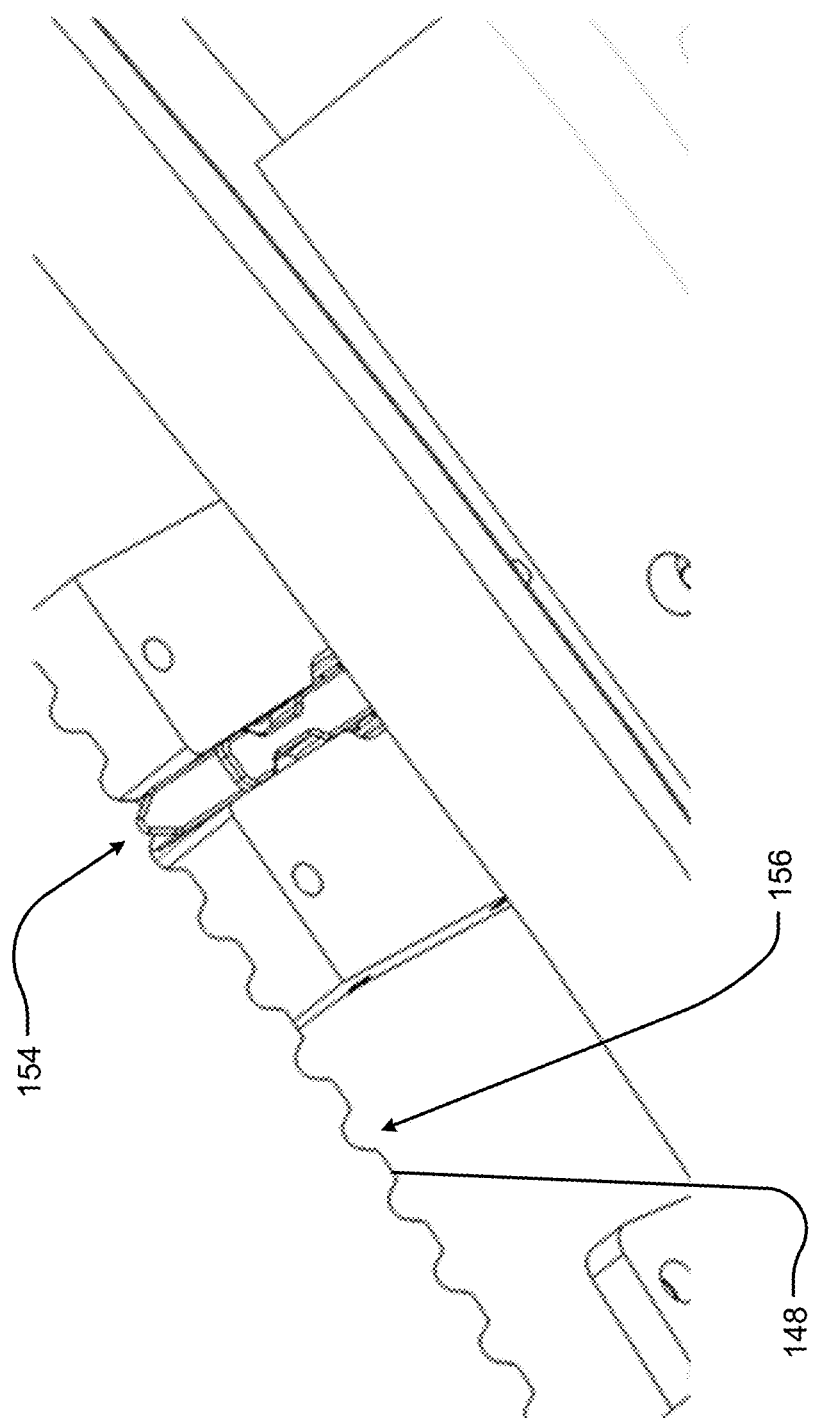
FIG. 5 is a detailed view of a spring loaded lever according to at least one embodiment of the present disclosure.
Figure 6:
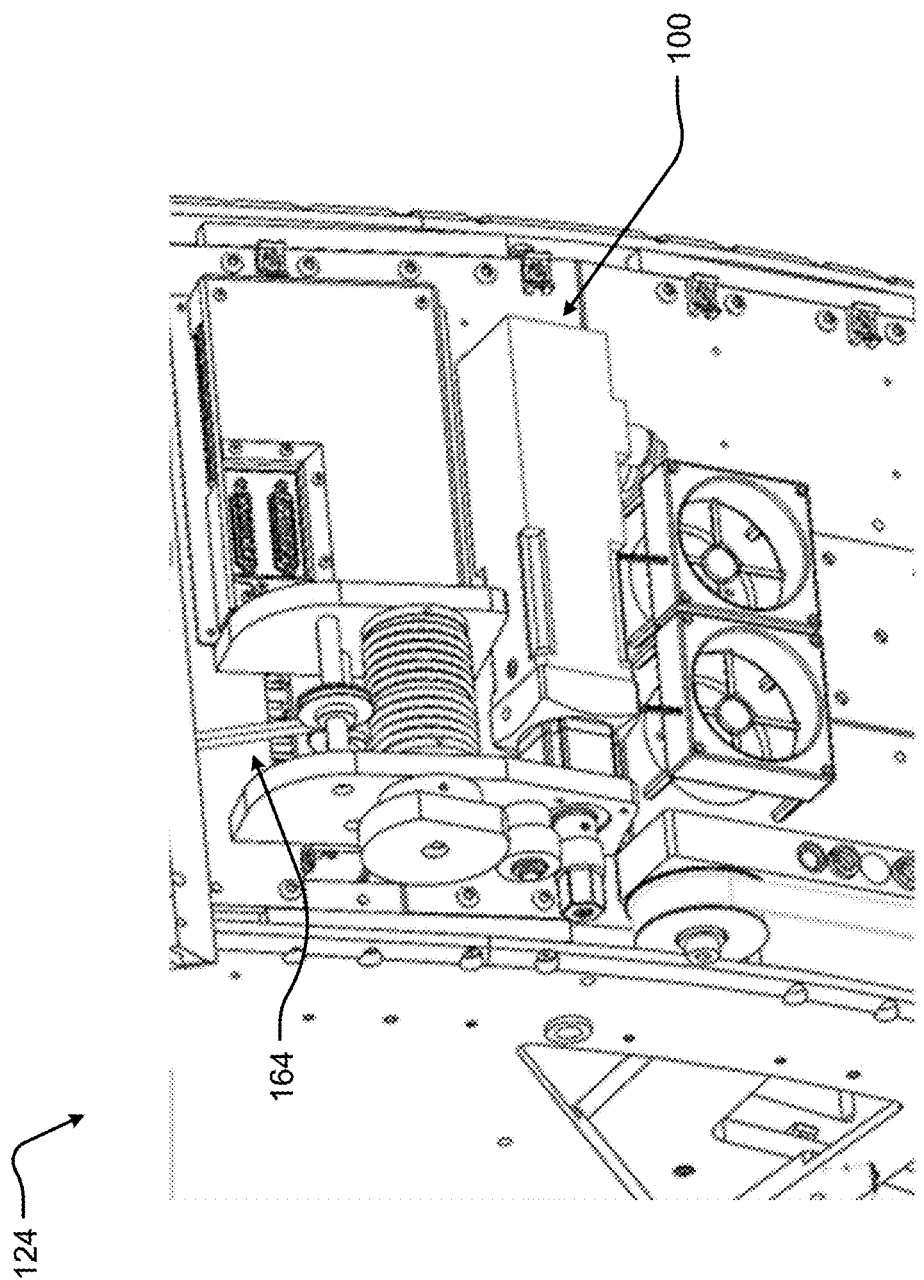
FIG. 6 is a detailed view of a winch drive according to at least one embodiment of the present disclosure.
Figure 7:
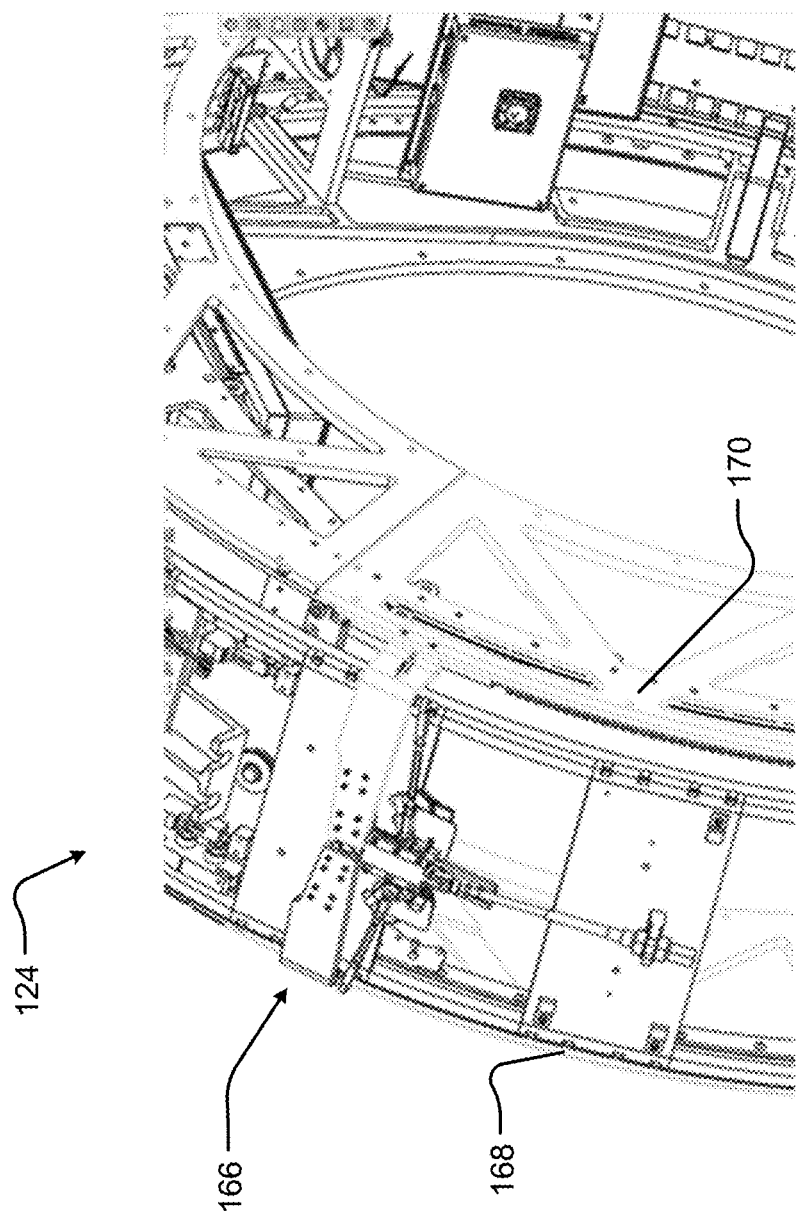
FIG. 7 is a detailed view of linear bearing mechanisms according to at least one embodiment of the present disclosure.

In the illustrated embodiment, a door 160 is telescoped and rotated about the gantry 104 using the sector gear 148 and a servo driven winch drive 162. The servo driven winch drive 162 comprises a pair of cables 164 in a push-pull arrangement with a pair of linear bearing mechanisms 166 (shown in FIG. 7). The pair of linear bearing mechanisms 166 control a motion of the door 160 in a first direction and a second direction. The first direction may be, for example, a lateral motion away from the gantry 104 and the second direction may be, for example, a telescoping motion over and on top of the gantry 104. As shown in FIG. 5, the first direction or lateral motion of the sector gear 148 also engages a spring-loaded lever 154 that locks or retains the sector gear 148 radially on the door 160 when the door 160 opens. More specifically, the spring-loaded lever 154 engages with sector gear teeth 156 of the sector gear 148. Such engagement enables the sector gear 148 to travel with the door 160.

Figure 8:
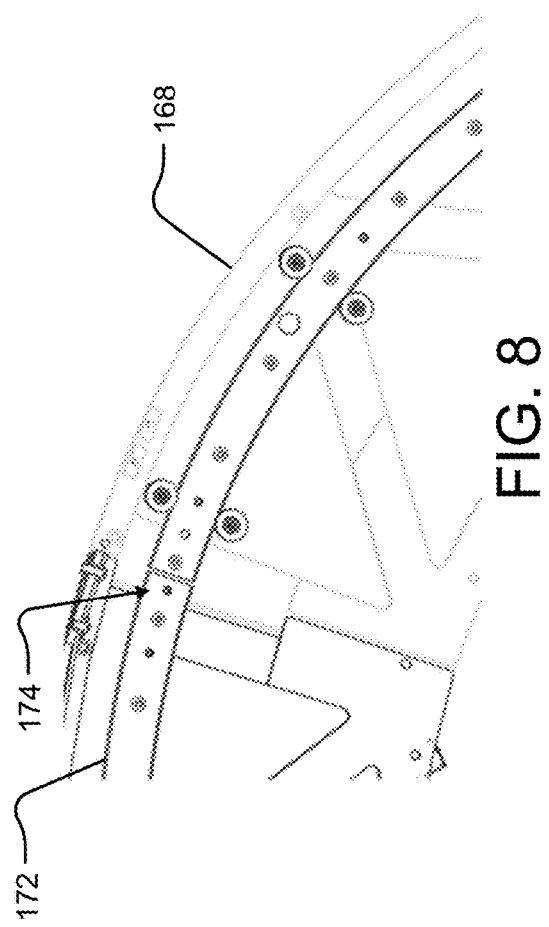
FIG. 8 is a detailed view of a door sidewall according to at least one embodiment of the present disclosure.

Turning to FIG. 8, the door 160 comprises a first sidewall 168 and a second sidewall 170 with the first sidewall 168 being integral with a rotor rail 172 mounted to the gantry 104. A plurality of pins 174 are configured to align at least one of the first sidewall 168 and the second sidewall 170 with the rotor rail 172. More specifically, the plurality of pins 174 at each end of the first sidewall 168 or the second sidewall 170 engages the rotor rail 172 as the door 160 closes. The winch drive 162 then retains or locks the first sidewall 168 or the second sidewall 170 in place by setting a brake on the winch drive 162.

Figure 9:
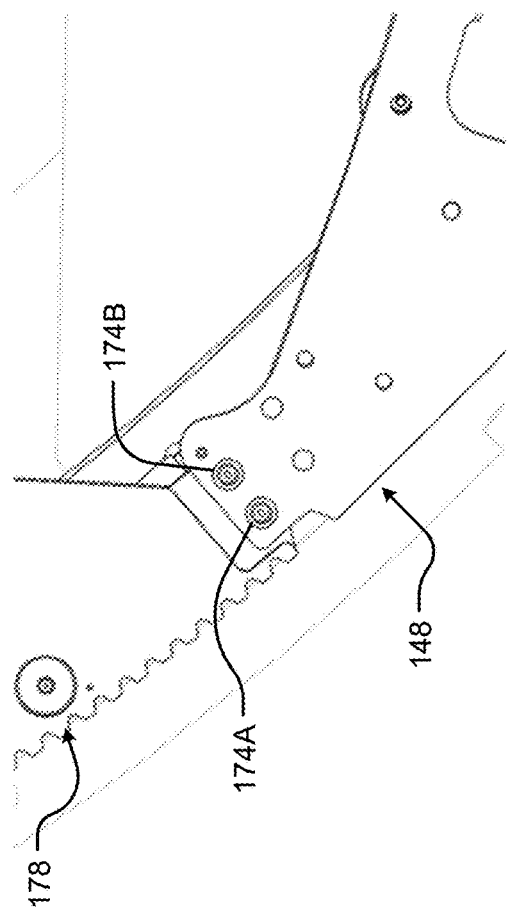
FIG. 9 is a detailed view of a sector gear according to at least one embodiment of the present disclosure.

Turning to FIG. 9, the sector gear 148 mounted to the rotor 124 is shown. Additional pins of the plurality of pins 174 may be configured to align the sector gear 148 to a rotor gear 178. More specifically, two pins 174A, 174B disposed at a top and a bottom of the sector gear 148 radially align the sector gear 148 with the rotor gear 178.

Figure 11:
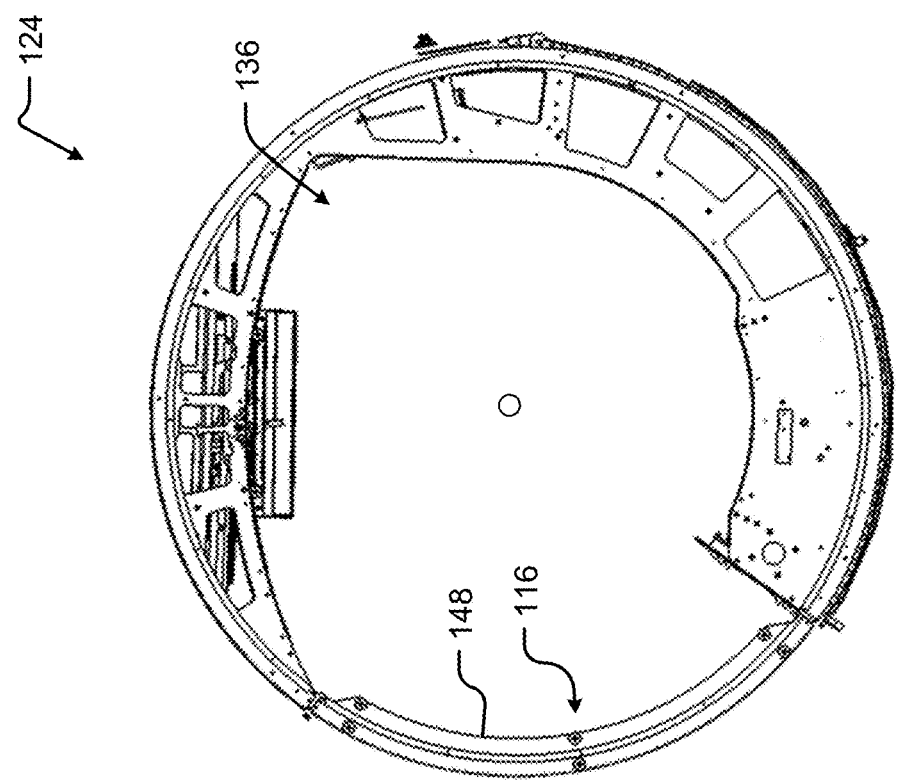
FIG. 11 is a front view of a rotor and a sector gear in a second position according to at least one embodiment of the present disclosure.
Figure 10:
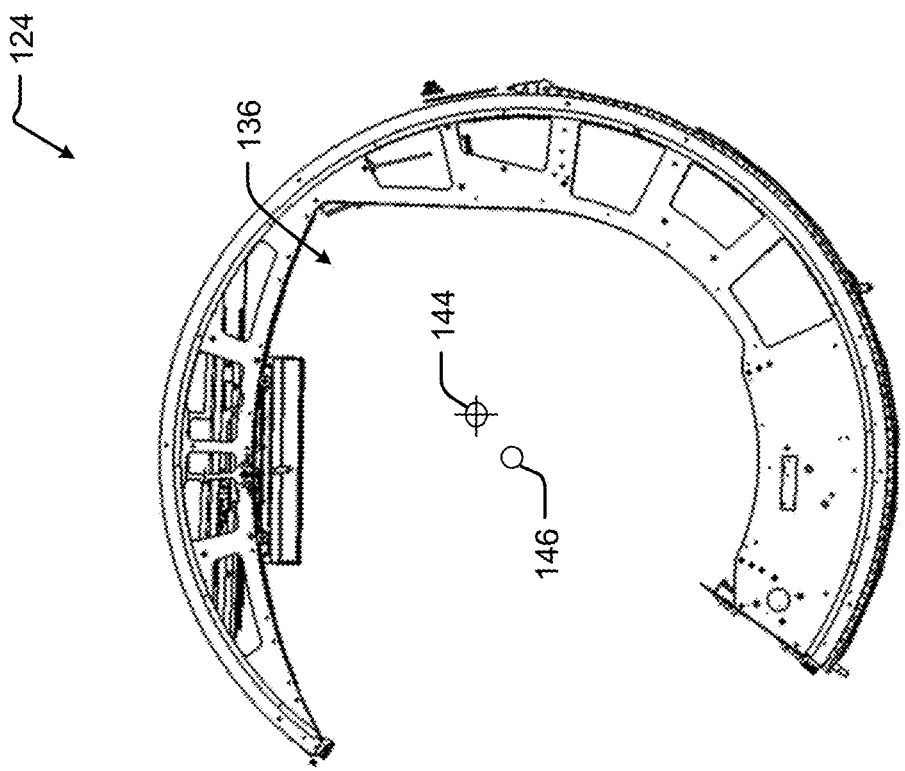
FIG. 10 is a front view of a rotor and a sector gear in a first position according to at least one embodiment of the present disclosure.

Turning to FIGS. 10 and 11, the rotor 124 and the sector gear 148 of the segment 116 in a first position and a second position are respectively shown. As previously described, the rotor 124 may cause the center of gravity 144 of the imaging device 100 to shift and be offset from the central axis 146 of the gantry ring. In some embodiments, one or more counterbalancing measures 150 may be integrated with or attached to one or more components of the imaging device 100 to counterbalance the rotor 124, thereby aligning the center of gravity 144 with the central axis 146 and the center of rotation.

Figure 12:
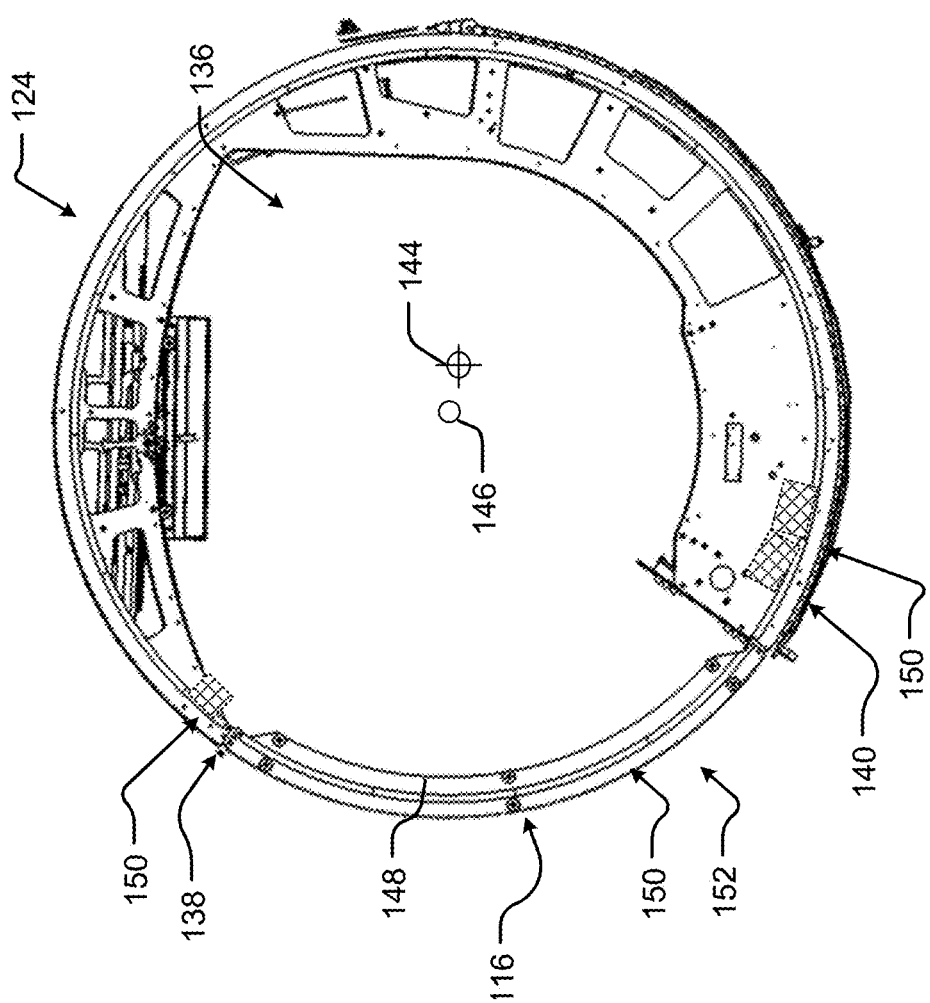
FIG. 12 is a front view of a rotor and a sector gear in the second position according to at least one embodiment of the present disclosure.

Turning to FIG. 12, the rotor 124 and a sector gear 148 are shown with the sector gear 148 in the second position. As shown, the center of gravity 144 of the imaging device 100 may shift towards or align with the central axis 146 using the one or more counterbalancing measures 150.

In some embodiments, the one or more counterbalancing measures 150 may be integrated with or attached to a portion 152 of the segment 116. In such embodiments, section(s) of or an entirely of the portion 152 may be formed of a heavier material (e.g., steel, tungsten, etc.) to act as a counterweight to the rotor 124, one or more weights may be attached to or integrated with the portion 152 to increase a weight of the portion 152, or a combination of the portion 152 is formed of a heavier material and one or more weights are attached to the portion 152. It will be appreciated that any material may be used to form the counterbalancing measures 150. In In some embodiments, the portion 152 may comprise the sector gear 148. In such embodiments, the sector gear 148 may be formed of a heavier material, one or more weights may be attached to or integrated with the sector gear 148, portions of the sector gear 148 may be formed of a heavier material, or at least a portion of the sector gear 148 may be formed of a heavier material and one or more weights may be attached to the sector gear 148. The sector gear 148, portions of the sector gear 148, and/or the one or more weights may comprise steel and/or tungsten. In such embodiments, when the sector gear 148 is attached to the gantry 104 wherein the sector gear 148 (and the door) closes the opening 134 to the gantry 104, the sector gear 148 acts as a counterweight to the rotor 124, thereby shifting or aligning the center of gravity 144 with central axis 146.

In some embodiments, the sector gear 148 may comprise a first sector gear and a second sector gear. In such embodiments, the first sector gear and/or the second sector gear may comprise the one or more counterbalancing measures 150. In embodiments where each of the first sector gear and the second sector gear includes the one or more counterbalancing measures 150, the first sector gear and the second sector gear may have the same counterbalancing measures 150, may have different counterbalancing measures 150, and/or may have any combination of counterbalancing measures 150. For example, the first sector gear may be formed of a first material such as, for example, steel, the second sector gear may be formed of a second material such as, for example, aluminum, and one or more weights may be attached to the second sector gear.

In other embodiments, the one or more counterbalancing measures 150 may comprise attaching or integrating one or more weights with the first end 138 and/or the second end 140 of the rotor 124 to counterbalance the rotor 124. Alternatively or additionally, one or more weights may be integrated with or attached to any portion of the rotor 124. It will be appreciated that the counterbalancing measures 150 may be added to or integrated with any component or any combination of component(s) of the imaging device 100. For example, the sector gear 148 may comprise one or more weights and each of the first end 138 and the second end 140 may be formed of a material such as, for example, steel. In another example, the door may comprise one or more weights attached to the door. It will also be appreciated that the one or more counterbalancing measures 150 may be used with any type of segment 116 such as, for example, a telescoping segment, a hinged segment, a vertical lift segment, etc.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A counterbalanced imaging device comprising:
a gantry ring having a central axis and an opening that provides access to the central axis, the gantry ring having an interior cavity contained therein;
a C-shaped rotor housed within the interior cavity, and rotatable around the central axis, wherein the C-shaped rotor causes the imaging device to have a center of gravity offset from the central axis of the gantry ring;
a detachable segment of the gantry ring that selectively covers the opening, wherein a portion of the detachable segment comprises one or more weights to counterbalance the C-shaped rotor thereby moving a center of gravity of the C-shaped rotor and the detachable segment towards the central axis of the gantry ring;
a drive mechanism secured to the C-shaped rotor, and adapted to rotate the C-shaped rotor around the interior of the gantry ring;
an imaging source secured to the C-shaped rotor at a first position; and
an imaging detector secured to the C-shaped rotor at a second position, opposite the imaging source on the gantry ring.

2. The counterbalanced imaging device of claim 1, wherein the detachable segment comprises a door and a sector gear, wherein the sector gear is configured to attach to the C-shaped rotor when the detachable segment is attached to the gantry ring and configured to attach to the door when the detachable segment is not attached to the gantry ring.

3. The counterbalanced imaging device of claim 2, wherein the portion of the detachable segment comprises the sector gear.

4. The counterbalanced imaging device of claim 3, wherein the sector gear comprises a first sector gear and a second sector gear.

5. The counterbalanced imaging device of claim 1, wherein the imaging source is configured to project radiation as the imaging source rotates about the central axis, and wherein the imaging detector is positioned to detect the projected radiation.

6. The counterbalanced imaging device of claim 1, wherein the gantry ring is configured to be positioned around an object to be imaged.

7. The counterbalanced imaging device of claim 1, wherein an object to be imaged may enter and exit the gantry ring through the opening.

8. The counterbalanced imaging device of claim 1, wherein the imaging source is an X-ray source.

9. The counterbalanced imaging device of claim 1, wherein the one or more weights are attached to the portion of the detachable segment.

10. The counterbalanced imaging device of claim 1, wherein the one or more weights are integrated with the portion of the detachable segment.

11. A counterbalanced imaging device comprising:
a gantry ring having a central axis and an opening that provides access to the central axis, the gantry ring having an interior cavity contained therein;
a detachable segment of the gantry ring that selectively covers the opening;
a C-shaped rotor housed within the interior cavity, and rotatable around the central axis, wherein the C-shaped rotor extends from a first end to a second end, and wherein each of the first end and the second end has one or more counterbalance measures contained therein to align a center of gravity of the C-shaped rotor with the center of rotation;
a drive mechanism secured to the C-shaped rotor, and adapted to rotate the C-shaped rotor around the interior of the gantry ring;
an imaging source secured to the C-shaped rotor at a first position; and
an imaging detector secured to C-shaped rotor at a second position, opposite the imaging source on the gantry ring.

12. The counterbalanced imaging device of claim 11, wherein the counterbalance measures comprise weights attached to each of the first end and the second end.

13. The counterbalanced imaging device of claim 11, wherein the counterbalance measures comprise weights integrated into each of the first end and the second end.

14. The counterbalanced imaging device of claim 11, wherein the imaging source is an X-ray source.

15. An imaging device, comprising:
an imaging source;
an imaging detector; and
a gantry ring that physically supports the imaging source and the imaging detector and that enables the imaging source and the imaging detector to simultaneously rotate about a center of rotation, wherein the gantry ring comprises a detachable segment having one or more counterbalance measures contained therein to align a center of gravity of the gantry ring with the center of rotation when the detachable segment is mounted onto the gantry ring.

16. The imaging device of claim 15, wherein the detachable segment comprises a door and a sector gear.

17. The imaging device of claim 16, wherein the counterbalanced measures comprise the sector gear.

18. The imaging device of claim 17, wherein the sector gear comprises a first sector gear and a second sector gear.

19. The imaging device of claim 18, wherein each of the first sector gear and the second sector gear comprises steel.

20. The imaging device of claim 15, wherein the imaging source is configured to project radiation as the imaging source rotates about the central axis, and wherein the imaging detector is positioned to detect the projected radiation.

* * * * *